(12) United States Patent
Kim

(10) Patent No.: US 7,125,545 B2
(45) Date of Patent: Oct. 24, 2006

(54) PERMANENT COSMETIC COMPOSITION FOR ONE-STEP PERMANENT OPERATION

(76) Inventor: Byung-Man Kim, 301-ho, #207-8, Banbon 2-dong, 435-042 Gunpo-si, Kyunggi-do (KR)

( * ) Notice: Subject to any disclaimer, the term of this patent is extended or adjusted under 35 U.S.C. 154(b) by 420 days.

(21) Appl. No.: 10/340,187

(22) Filed: Jan. 10, 2003

(65) Prior Publication Data

US 2003/0170192 A1  Sep. 11, 2003

(30) Foreign Application Priority Data

Jan. 18, 2002  (KR) .................. 10-2002-0003088

(51) Int. Cl.
*A61K 7/09* (2006.01)
*A61K 7/11* (2006.01)

(52) U.S. Cl. .................. 424/70.2; 424/70.1; 424/70.4; 424/70.5; 424/70.51

(58) Field of Classification Search ............... 424/70.2, 424/70.5; 514/707
See application file for complete search history.

(56) References Cited

U.S. PATENT DOCUMENTS 4,192,863 A    3/1980  Kondo
4,659,566 A  *  4/1987  Petrow ................. 424/70.5
4,832,948 A  *  5/1989  Kondo ................. 424/70.5

* cited by examiner

*Primary Examiner*—Sreeni Padmanabhan
*Assistant Examiner*—Gina C. Yu
(74) *Attorney, Agent, or Firm*—Hunton & Williams LLP

(57) ABSTRACT

Disclosed is a one-step permanent cosmetic composition that comprises 1.0 to 5.5 wt. % of a reducing agent; 0.1 to 9.5 wt. % of an alkaline agent; 0.1 to 7.0 wt. % of a catalyst; 1.0 to 15.0 wt. % of an alcohol; and distilled water or ion exchange water for the residual percentage by weight, using a solvent having an alkalinity (representing a consumption of 0.01 N HCl for 1 mL of a test sample) of 1.0 to 4.6 and having a pH value of less than 9.6; and also a one-step permanent cosmetic composition that comprises 1.0 to 5.5 wt. % of a reducing agent; 0.1 to 9.5 wt. % of an alkaline agent; 0.1 to 7.0 wt. % of a catalyst; 1.0 to 15.0 wt. % of an alcohol and additionally 1.0 to 4.5 wt. % of a viscosity enhancing agent; and distilled water or ion exchange water for the residual percentage by weight, using a solvent having an alkalinity (representing a consumption of 0.01 N HCl for 1 mL of a test sample) of 1.0 to 4.6 and having a pH value of less than 9.6.

1 Claim, No Drawings

PERMANENT COSMETIC COMPOSITION FOR ONE-STEP PERMANENT OPERATION

This patent application claims priority of Korean Patent Application No. 10-2002-0003088, which was filed on Jan. 18, 2002. This application is also related to PCT International Application No. PCT/KR02/02470, which was filed on Dec. 28, 2002.

SUMMARY OF THE INVENTION

The present invention relates to a permanent cosmetic composition for a one-step permanent waving operation (hereinafter referred to as "one-step permanent cosmetic composition"), which comprises 1.0 to 5.5% by weight of a reducing agent, 0.1 to 9.5% by weight of an alkaline agent, 0.1 to 7.0% by weight of a catalyst, 1.0 to 15.0% by weight of an alcohol, and the balance of distilled water or ion exchanged water, and has an alkalinity of 1.0 to 4.6 as measured in a consumption (mL) of 0.01 N HCl per 1 mL of test sample, and a pH value of less than 9.6. The one-step permanent cosmetic composition of the present invention is preferably a permanent wave solution for a one-step permanent waving operation (hereinafter referred to as "one-step permanent cosmetic solution").

The present invention also relates to a one-step permanent cosmetic composition, which comprises 1.0 to 5.5% by weight of a reducing agent, 0.1 to 9.5% by weight of an alkaline agent, 0.1 to 7.0% by weight of a catalyst, 1.0 to 15.0% by weight of an alcohol, 1.0 to 4.5% by weight of a thickener, and the balance of distilled water or ion exchanged water, and has an alkalinity of 1.0 to 4.6 as measured in a consumption (mL) of 0.01 N HCl per 1 mL of test sample, and a pH value of less than 9.6. The one-step permanent cosmetic composition of the present invention is preferably a permanent straightening cream for a one-step permanent straightening operation (hereinafter referred to as "one-step permanent straightening cream").

BACKGROUND OF THE INVENTION

The present invention relates to the one-step permanent wave solution, which contains no neutralizing agent. Conventional permanent wave solutions were used in a two-step process. Such two-step permanent wave solutions mainly consist of a reducing solution as a first solution comprising ammonium thioglycolate and an alkaline agent such as ammonia water; and an oxidizing solution as a second solution (so-called "neutralizing agent") comprising peroxide or sodium bromide.

These two-step permanent wave solutions have the following several problems. First, repeated use of a reducing agent with high alkalinity and a strong oxidizing agent results in de-coloration or damage to the hair as well as irritations to the skin when they are in contact with the skin. Second, ammonium thioglycolate and ammonia water emit repulsive odors, which remain for a long period, even after hair washing, thereby causing discomfort. Third, treatment with a neutralizing agent causes the inconvenience of having to undergo a two-step process, and the solution drips during the permanent waving, causing irritations to skin and damage to clothing.

The reaction mechanism of the conventional two-step permanent wave solution will now be described briefly. Korean Patent No. 134,755 discloses the two-step permanent wave solution. As disclosed in this patent, the R—S—S—R bond of cystine contained in keratin, a constituent of hair, is first broken into R—S—H and H—S—R by a hydrogenation reduction reaction, and then re-bonded by means of an oxidizing agent as illustrated in the following reaction equation in a state where the hair was deformed into curls. Thus, the hair curls are stabilized.

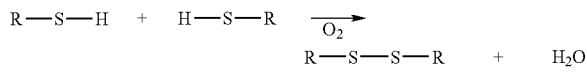

Furthermore, the conventional permanent wave solution is composed of a first solution containing an excess of an alkali compound (e.g., alkali carbonate, caustic alkali, or ammonia water) that has an alkalinity of more than 3.5 as measured in the amount of 0.1N HCl (mL) required for neutralizing 1 mL of the associated alkali. So, applying the first solution onto hair immediately forms a cyanide compound (e.g., potassium cyanide). This cyanide compound functions to break the —S—S— bond of cystine. More specifically, the reaction between cystine (R—S—S—R where R represents keratin) and potassium cyanide (KCN) occurs in two steps as shown in the following reaction equations (i) and (ii):

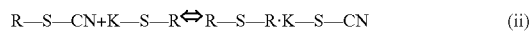

As described above, this reaction produces lanthionine R—S—R and potassium thiocyanide (see C. R. Robbins, "Chemical and Physical Behavior of Human Hair," Fragrance Journal, p. 56, 1982). Subsequently, as can be seen in the following chemical equation (iii), when using the second solution, thiocyanide (—SCN) is oxidized by alkali bromide, which is an oxidizing agent principally contained in the second solution. Even when the second solution is not used, cyanide (ferric cyanide), which is a byproduct in the waste solution of the permanent wave solution, is oxidized to yield a cyanide compound.

As is well known in the art, the cyanide compound reacts with iron contained in hair to form a ferrous hexacyano compound (blue cyanide) or a ferric hexacyano compound (red cyanide).

Besides the above problems, the one-step permanent wave solution, which was recently developed but rarely used, has problems in that the formation of hair curl during the permanent waving is very slow and the curls after the permanent waving readily gets loose by hair washing, thereby deteriorating the product quality.

Accordingly, it is an object of the present invention to solve the problems with the prior art and to provide a one-step permanent wave solution that eliminates the need for using a neutralizing agent during a permanent waving operation, simplifies the permanent wave operation into one step, reduces potential discomfort from contact with the skin, prevents hair damage, makes hair glossy and elastic without odor and provides a pleasant operation condition for the permanent waving.

DETAILED DESCRIPTION OF THE INVENTION

In order to accomplish the above object, in one embodiment, the present invention provides a one-step permanent wave solution, which comprises 1.0 to 5.5% by weight of a reducing agent, 0.1 to 9.5% by weight of an alkaline agent, 0.1 to 7.0% by weight of a catalyst, 1.0 to 15.0% by weight of an alcohol, and the balance of distilled water or ion exchanged water, and has an alkalinity of 1.0 to 4.6 as measured in a consumption (mL) of 0.01 N HCl per 1 mL of test sample), and a pH value of less than 9.6. The one-step permanent cosmetic composition of the present invention is preferably a one-step permanent wave solution.

In another embodiment, the present invention provides a one-step permanent wave solution, which comprises 1.0 to 5.5% by weight of a reducing agent, 0.1 to 9.5% by weight of an alkaline agent, 0.1 to 7.0% by weight of a catalyst, 1.0 to 15.0% by weight of an alcohol, 1.0 to 4.5% by weight of a thickener, and the balance of distilled water or ion exchanged water, and has an alkalinity of 1.0 to 4.6 as measured in a consumption (mL) of 0.01 N HCl per 1 mL of test sample, and a pH value of less than 9.6. The one-step permanent cosmetic composition is preferably a one-step permanent straightening cream.

The reducing agent as used in the present invention is preferably at least one selected from the group consisting of thioglycolic acid, thioacetic acid, thioglycerol and keratin hydrolysates.

The alkaline agent as used in the present invention is preferably at least one selected from the group consisting of monoethanol amine, diethanol amine, triethanol amine, sodium hydroxide, potassium hydroxide, sodium carbonate and potassium carbonate.

The catalyst as used in the present invention is preferably at least one selected from the group consisting of potassium thiocyanide (KSCN), sodium thiocyanide (NaSCN), potassium ferricyanide ($K_3[Fe(CN)_6]$) and potassium ferrocyanide ($K_4[Fe(CN)_6]$).

The alcohol as used in the present invention is preferably at least one selected from the group consisting of ethyl alcohol, propyl alcohol, benzyl alcohol and polyalcohol.

The reducing agent as used in the present invention is preferably selected from thioglycolic acid, thioacetic acid, thioglycerol and keratin hydrolysates. The content of the reducing agent in the composition is 1.0 to 5.5% by weight. The alkaline agent as used in the present invention is preferably selected from mono-, di- or tri-ethanol amine, sodium hydroxide, potassium hydroxide, sodium carbonate and potassium carbonate. The content of the alkaline agent in the composition is 0.1 to 9.5% by weight. The catalyst as used in the present invention is preferably selected from potassium thiocyanide (KSCN), sodium thiocyanide (NaSCN), potassium ferricyanide ($K_3[Fe(CN)_6]$) and potassium ferrocyanide ($K_4[Fe(CN)_6]$). The content of the catalyst in the composition is 0.1 to 5.0% by weight. The alcohol as used in the composition of the present invention is preferably selected from ethyl alcohol, propyl alcohol, benzyl alcohol and polyalcohol. The content of the alcohol in the composition is 1.0 to 15.0% by weight. The residual content of the composition includes a thickener and distilled water or ion exchanged water. The permanent wave solution has an alkalinity of 1.0 to 4.6 as measured in a consumption (mL) of 0.01 N HCl per 1 mL of test sample), and a pH value of less than 9.6.

By the one-step permanent wave solution of the present invention as described above involves, as well as the M—SCN reaction, the —S—S— bond of cystine is hydrolyzed with the reducing agent in the alkaline solution and, during or after hair drying, subjected to slow dehydration and spontaneous oxidization reactions to produce the —S—S— bond again.

The hydrolysis and dehydration reactions can be expressed as follows.

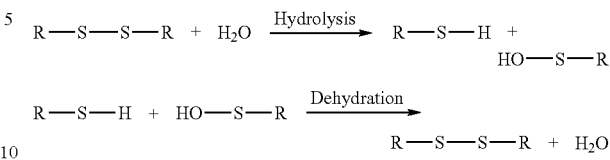

Mechanism of Reduction and Spontaneous Oxidation

The —S—S— bond of cystine in hair keratin is subjected to reduction reaction with the reducing agent and spontaneous oxidation reaction, as shown in the following reaction equations:

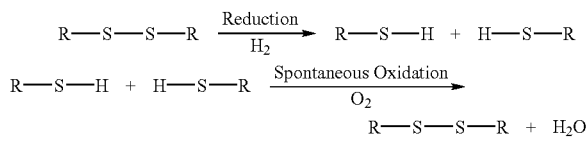

As described above, the one-step permanent wave solution of the present invention involves three reactions, including catalysis, hydrolysis/dehydration and reduction/oxidation, that occur in a mutual and simultaneous manner. Hence, the one-step permanent wave solution of the present invention has a reaction rate of more than 95%, whereas the two-step permanent wave solution of the prior art has the reaction rate of about 60 to 70%. As a result, the one-step permanent wave solution of the present invention is higher than the two-step permanent wave solution in terms of the reaction rate, thereby greatly reducing hair damage, rapidly making hair curl and maintaining significant hair elasticity.

In addition, in order to prevent the reaction of cyanide with iron (Fe) contained in hair, the activity of iron is suppressed by a chelating agent, thereby inhibiting the formation of an iron-cyanide complex.

The present invention is superior to the conventional two-step permanent wave solutions or the recently developed but rarely used one-step permanent wave solution in curling hair without using an oxidizing agent and in creating long lasting curls. The present invention creates natural and glossy hair without a repulsive odor and without damage to the hair and allows for very convenient and easy permanent waving.

In the one-step permanent wave solution of the present invention, the cyanide produced in the reaction mechanism of the conventional two-step permanent wave solution functions to break the —S—S— bond of cystine, and the aqueous soluble M—SCN ingredient added as a catalyst induces the reaction represented by the following reaction equation to temporarily form the —S—S— bond of cystine and to finish the hair curl without using a neutralizing agent (i.e., the second agent in the two-step permanent wave solution—sodium bromide or hydrogen peroxide).⇔ where M denotes a metal element such as K, Na or Fe.

As described above, the induction of chemical equilibrium either prevents or rapidly decreases the yield of the production of lanthionine R—S—R in the one-step permanent wave solution. The residual M—SCN is readily removed during washing of hair so that the re-bonded R—S—S—R is increased and stabilized due to chemical equilibrium shift. So, the M—SCN, which rapidly dissolves in water, rarely remains on hair, thereby causing no secondary problems.

When using the permanent wave solution of the present invention, hair treatment with a neutralizing agent as in the case of using the two-step permanent wave solution is not needed. More specifically, hair is cleaned with a shampoo, vigorously towel dried, applied with the permanent wave solution of the present invention, rolled with rods and applied with the permanent wave solution again. Subsequently, after being covered with a vinyl cover, the hair is heat-treated with an electric cap or infrared radiator for 15 to 20 minutes. Then, test curling is performed after about 30 minutes. Subsequently, the hair is left for 15 minutes with the vinyl cover removed. Next, the rods are removed from the hair, which is then washed with water and immediately dried. In this method, the permanent waving may be carried out in such a manner that the hair is rolled with rods and left as is, without being covered with a vinyl cover or heat-treated, in which case the process of permanent waving may be only a little more delayed.

The present invention will now be described in detail in connection with preferred embodiments, which are not intended to limit the scope of the present invention.

EXAMPLES

Example 1

| | |
|---|---|
| Thioglycerol | 3.0% by weight |
| Ethanol | 3.0% by weight |
| EDTA 2Na | 0.4% by weight |
| Ammonium sulfate | 0.1% by weight |
| Potassium thiocyanide | 0.7% by weight |
| Sodium carbonate | 0.7% by weight |
| Others (thickener and distilled water) | 92.1% by weight |

Example 2

The composition is the same as described in Example 1, except that it includes 1.5% by weight of sodium thiocyanide instead of potassium thiocyanide and 91.3% by weight of distilled water.

Example 3

The composition is the same as described in Example 1, except that it includes 3.7% by weight of thioglycolic acid instead of thioglycerol and 91.4% by weight of distilled water.

Example 4

The composition is the same as described in Example 1, except that it includes 4.0% by weight of thioacetic acid instead of thioglycerol and 91.1% by weight of distilled water.

Example 5

The composition is the same as described in Example 1, except that it includes 0.9% by weight of potassium hydroxide (KOH) instead of sodium carbonate and 91.9% by weight of distilled water.

Example 6

The composition is the same as described in Example 1, except that it includes 0.6% by weight of sodium hydroxide (NaOH) instead of sodium carbonate and 92.2% by weight of distilled water.

Example 7

The composition is the same as described in Example 1, except that it includes 1.0% by weight of triethanol amine instead of sodium carbonate and 91.8% by weight of distilled water.

Example 8

The composition is the same as described in Example 1, except that it includes 6.0% by weight of polyethylene glycol #400 (PEG #400) instead of ethanol and 89.1% by weight of distilled water.

| | |
|---|---|
| Comparative Example 1 | |
| Ammonium thioglycolate | 3.0% by weight |
| 28% ammonia water | 3.7% by weight |
| Ammonium sulfate | 0.1% by weight |
| Tartaric acid | 0.15% by weight |
| Potassium hydroxide | 0.07% by weight |
| Monoethanol amine | 0.5% by weight |
| Ethanol | 1.0% by weight |
| Distilled water | 91.48% by weight |
| Comparative Example 2 | |
| Ammonium thioglycolate | 3.3% by weight |
| 28% ammonia water | 1.0% by weight |
| Sodium carbonate | 1.7% by weight |
| Citric acid | 1.15% by weight |
| Potassium hydroxide | 0.5% by weight |
| Triethanol amine | 0.1% by weight |
| Ethanol | 1.0% by weight |
| Distilled water | 91.25% by weight |

In order to test the one-step permanent wave solution of the present invention, hair was washed with shampoo, towel dried, applied with the permanent wave solution, rolled with rods and applied with the permanent wave solution again. Subsequently, after being covered with a vinyl cover, the hair was heat-treated with an electric cap for 15 minutes. After the hair was left for 30 minutes with the electric cap removed, the vinyl cover was removed. Next, after the hair was left again for 15 minutes with the vinyl cover removed, the rods were removed from the hair for sufficient rinsing with water.

Then a hair beauty specialist performed a sensory evaluation on the condition of the hair following the above test of the examples and the comparative examples. The results are presented in Table 1. The evaluation criteria range from a score of 10 (good or none) to a score of 0 (bad or severe).

TABLE 1

| Test Item | Comparative Examples 1 | Comparative Examples 2 | Examples 1 | Examples 2 | Examples 3 | Examples 4 | Examples 5 | Examples 6 | Examples 7 | Examples 8 |
|---|---|---|---|---|---|---|---|---|---|---|
| A | 9 | 8 | 10 | 10 | 9 | 10 | 9 | 9 | 10 | 9 |
| B | 6 | 4 | 9 | 9 | 8 | 10 | 8 | 8 | 10 | 9 |
| C | 7 | 5 | 9 | 9 | 7 | 9 | 9 | 9 | 9 | 9 |
| D | 1 | 4 | 10 | 10 | 10 | 10 | 10 | 10 | 10 | 10 |
| E | 6 | 6 | 9 | 9 | 8 | 10 | 9 | 9 | 10 | 10 |
| F | None | None | None | None | None | None | None | None | None | None |
| G | 8 | 8 | 8 | 9 | 8 | 10 | 8 | 8 | 9 | 10 |

Note)
A: Curl strength (in early stage)
B: Curl strength (after washing hair three times)
C: Smell of thio compound
D: Smell of ammonia
E: Residual smell after hair washing
F: De-coloration
G: Hair damage Example 9

| | |
|---|---|
| Thioglycerol | 3.0% by weight |
| Ethanol | 3.0% by weight |
| EDTA 2Na | 0.4% by weight |
| Ammonium sulfate | 0.1% by weight |
| Potassium thiocyanide | 0.7% by weight |
| Sodium carbonate | 0.7% by weight |
| HPMC#40,000 | 2.0% by weight |
| Others (thickener and distilled water) | 90.1% by weight |

Example 10

The composition is the same as described in Example 9, except that it includes 1.5% by weight of sodium thiocyanide instead of potassium thiocyanide and 89.3% by weight of distilled water.

Example 11

The composition is the same as described in Example 9, except that it includes 3.7% by weight of thioglycolic acid instead of thioglycerol and 89.4% by weight of distilled water.

Example 12

The composition is the same as described in Example 9, except that it includes 4.0% by weight of thioacetic acid instead of thioglycerol and 89.1% by weight of distilled water.

Example 13

The composition is the same as described in Example 9, except that it includes 0.9% by weight of potassium hydroxide (KOH) instead of sodium carbonate and 89.9% by weight of distilled water.

Example 14

The composition is the same as described in Example 9, except that it includes 3.0% by weight of humed silica #200 instead of HPMC#40,000 and 89.2% by weight of distilled water.

Example 15

The composition is the same as described in Example 9, except that it includes 1.0% by weight of triethanol amine instead of sodium carbonate and 89.8% by weight of distilled water.

Example 16

The composition is the same as described in Example 9, except that it includes 6.0% by weight of polyethylene glycol #400 (PEG #400) instead of ethanol and 87.1% by weight of distilled water.

| Comparative Example 3 | |
|---|---|
| Ammonium thioglycolate | 3.0% by weight |
| 28% ammonia water | 3.7% by weight |
| Ammonium sulfate | 0.1% by weight |
| Tartaric acid | 0.15% by weight |
| Potassium hydroxide | 0.07% by weight |
| Monoethanol amine | 0.5% by weight |
| Ethanol | 1.0% by weight |
| CMC | 4.0% by weight |
| Distilled water | 87.48% by weight |
| Comparative Example 4 | |
| Ammonium thioglycolate | 3.3% by weight |
| 28% ammonia water | 1.0% by weight |
| Sodium carbonate | 1.7% by weight |
| Citric acid | 1.15% by weight |
| Potassium hydroxide | 0.5% by weight |
| Triethanol amine | 0.1% by weight |
| Ethanol | 1.0% by weight |
| CMC | 4.0% by weight |
| Distilled water | 87.25% by weight |

In order to test the one-step permanent straightening cream of the present invention, hair was washed with shampoo, vigorously towel dried, uniformly applied with the permanent straightening cream, spread on a straightening plate and heat-treated for 20 minutes. After being left for 30 minutes as is, the hair was washed out. The hair was then left as is without being shampooed or tied for three days, thereby completing the straightened permanent hairstyle.

A hair beauty specialist performed a sensory evaluation on the condition of the hair following the above test of the examples and the comparative examples. The results are presented in Table 2. The evaluation criteria range from a score of 10 (good or none) to a score of 0 (bad or severe).

TABLE 2

| Test Item | Comparative Examples | | Examples | | | | | | | |
|---|---|---|---|---|---|---|---|---|---|---|
| | 3 | 4 | 9 | 10 | 11 | 12 | 13 | 14 | 15 | 16 |
| A | 9 | 8 | 10 | 10 | 9 | 10 | 9 | 9 | 10 | 9 |
| B | 6 | 4 | 9 | 9 | 8 | 10 | 8 | 8 | 10 | 9 |
| C | 7 | 5 | 9 | 9 | 7 | 9 | 9 | 9 | 9 | 9 |
| D | 1 | 4 | 10 | 10 | 10 | 10 | 10 | 10 | 10 | 10 |
| E | 6 | 6 | 9 | 9 | 8 | 10 | 9 | 9 | 10 | 10 |
| F | None | None | None | None | None | None | None | None | None | None |
| G | 8 | 8 | 8 | 9 | 8 | 10 | 8 | 8 | 9 | 10 |

Note)
A: Straightness (in early stage)
B: Straightness (after washing hair three times)
C: Smell of thio compound
D: Smell of ammonia
E: Residual smell after hair washing
F: De-coloration
G: Hair damage The one-step permanent cosmetic composition of the present invention reduces the required time for a permanent waving operation, simplifies the permanent weaving operation into one step, eliminates the need for using a neutralizing agent to prevent hair damage and any discomfort induced from contact with the skin, makes hair glossy and elastic and leaves no damage or smell on hair, thereby providing a pleasant operation condition for permanent waving and no remaining smell even after the permanent weaving.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A one-step permanent cosmetic composition which comprises 1.0 to 5.5% by weight of a reducing agent, 0.1 to 9.5% by weight of an alkaline agent, 0.1 to 7.0% by weight of a catalyst, 1.0 to 15.0% by weight of an alcohol and the balance of distilled water or ion exchanged water, and has an alkalinity of 1.0 to 4.6 as measured in a consumption (mL) of 0.01 N HCl per 1 mL of test sample, and a pH value of 7.0 to 9.6, characterized in that the said catalyst is at least one selected from the group consisting of potassium thiocyanide (KSCN) and sodium thiocyanide (NaSCN), wherein the said reducing agent is selected from thioglycolic acid, thioacetic acid, thioglycerol and keratin hydrolysates.

* * * * *